United States Patent
Vyas et al.

(10) Patent No.: US 9,744,359 B2
(45) Date of Patent: *Aug. 29, 2017

(54) APPARATUS AND METHOD FOR VISUAL STIMULATION INDICATION

(71) Applicant: Second Sight Medical Products, Inc., Sylmar, CA (US)

(72) Inventors: Neha Vyas, San Jose, CA (US); Robert J. Greenberg, Los Angeles, CA (US); Arup Roy, Valencia, CA (US); Donald Webber, Encino, CA (US); Richard Agustin Castro, Santa Monica, CA (US); John Reinhold, Tarzana, CA (US); Kelly McClure, Simi Valley, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/179,725

(22) Filed: Jun. 10, 2016

(65) Prior Publication Data

US 2016/0279416 A1 Sep. 29, 2016

Related U.S. Application Data

(63) Continuation of application No. 11/880,010, filed on Jul. 19, 2007, now Pat. No. 9,387,324.

(51) Int. Cl.
| A61N 1/08 | (2006.01) |
| A61N 1/36 | (2006.01) |
| A61N 1/372 | (2006.01) |
| G09B 21/00 | (2006.01) |
| G09B 23/28 | (2006.01) |
| A61N 1/05 | (2006.01) |

(52) U.S. Cl.
CPC ....... *A61N 1/36046* (2013.01); *A61N 1/0543* (2013.01); *A61N 1/37241* (2013.01); *A61N 1/37247* (2013.01); *G09B 21/00* (2013.01); *G09B 23/28* (2013.01)

(58) Field of Classification Search
None
See application file for complete search history.

(56) References Cited

U.S. PATENT DOCUMENTS

| 5,109,844 A | 5/1992 | de Juan, Jr. et al. |
| 5,935,155 A | 8/1999 | Humayun et al. |
| 5,944,747 A | 8/1999 | Greenberg et al. |

(Continued)

FOREIGN PATENT DOCUMENTS

WO  WO 00/56393 A  9/2000

OTHER PUBLICATIONS

Wentai Liu, et al., Image Processing and Interface for Retinal Visual Prostheses; Circuits & Systems, 2005; IEEE Int. Symp. On Kobe, Japan; May 25, 2003; pp. 2927-2930.

(Continued)

*Primary Examiner* — Erica Lee
(74) *Attorney, Agent, or Firm* — Scott Dunbar

(57) ABSTRACT

Methods and devices for verifying that proper visual stimulation is applied to the visual prostheses are described. In one of the methods, a visual stimulation system implanted on a subject is simulated externally. An external testing device is also discussed.

20 Claims, 13 Drawing Sheets

(56) References Cited

U.S. PATENT DOCUMENTS

| | | | |
|---|---|---|---|
| 6,400,989 B1 | 6/2002 | Eckmiller | |
| 6,458,157 B1 | 10/2002 | Suaning | |
| 6,718,209 B2 | 4/2004 | Williamson et al. | |
| 6,974,533 B2 | 12/2005 | Zhou | |
| 8,306,625 B2 * | 11/2012 | Vyas | A61N 1/36046 607/139 |
| 9,387,324 B2 * | 7/2016 | Vyas | A61N 1/36046 |
| 2004/0236389 A1 | 11/2004 | Fink et al. | |
| 2005/0201585 A1 | 9/2005 | Jannard et al. | |
| 2005/0222624 A1 | 10/2005 | Greenberg et al. | |
| 2006/0129207 A1 | 6/2006 | Fried et al. | |

OTHER PUBLICATIONS

Robert W. Thompson, Jr., et al.; Facial Recogiition Using Simulated Prosthetic Pixelized Vision Database Medline (online); US Nat. Library of medicine, Bethesda, MD; Nov. 2003.

J.F. Harvey; Visual Cortex Stimulator Prototype Based on Mixed-Signal Technology Devices; (online); 4th Ann, Conf. Of the Int. FES Society, Sendai, Japan Aug. 23-27, 1999, 4 pg.

* cited by examiner

APPARATUS AND METHOD FOR VISUAL STIMULATION INDICATION

CROSS REFERENCE TO RELATED APPLICATIONS

This application is a continuation application of U.S. patent application Ser. No. 11/880,010, filed Jul. 19, 2007 and issued as U.S. Pat. No. 9,387,324, for Apparatus and Method for Visual Stimulation Indication, which claims the benefit of U.S. provisional Patent Application Ser. No. 60/832,231, filed Jul. 20, 2006 for Apparatus and Method for Visual Stimulation Indication, the disclosures of which are incorporated herein by reference.

FEDERALLY SPONSORED RESEARCH OR DEVELOPMENT

The present invention was made with support from the United States Government under Grant number R24EY12893-01, awarded by the National Institutes of Health. The United States Government has certain rights in the invention.

FIELD

The present disclosure relates to visual prostheses. More particularly, the present disclosure relates to verifying that proper visual stimulation is applied to the visual prostheses.

BACKGROUND

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular visual prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretial). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a visual prosthesis for use with the flat retinal array described in de Juan.

In outer retinal degeneration, such as retinitis pigmentosa (RP), the photoreceptors and their supporting retinal pigment epithelium are impaired. In RP (incidence 1:4000) legal blindness is reached after 25 years. In many RP patients over sixty years of age, elementary vision with only gross movement or bright light perception remains, with little or no appreciable peripheral vision. Eventually, even light perception may recede. Currently, there is no treatment that stops or reverses the loss of photoreceptors in retinitis pigmentosa.

Traditionally, the approach to vision rehabilitation in subjects with retinitis pigmentosa has been to use the remaining vision with optical aides. If no useful vision is achieved, auditory or tactile information is substituted (e.g. Braille, cane travel, etc.). Attempts to remedy or alleviate vision loss have been made by replacing damaged cells or by electrically stimulating an undamaged proximal level, bypassing impaired cells. Replacement of damaged photoreceptors has been studied in animals through transplantation. Although there are indications that transplanted photoreceptors can make functional connections, many questions remain about the optimal methods to achieve long term graft survival and functionality in a human eye.

More recently, visual prostheses have been developed to address the extreme low vision population with retinal degeneration. Electrical stimulation at the primary visual cortex has been attempted and has the advantage of not requiring a viable optic nerve. However, such cortical stimulation has its own risks, such as exposing the brain to surgical complication and infection.

Stimulation at more distal neuronal locations has received recent attention and may provide an alternative in an outer retinal degenerative disease such as retinitis pigmentosa. Electrical stimulation of the optic nerve has been used to elicit a sensation of streaks or dots (phosphenes). Also, electrical stimulation through a contact lens electrode elicits phosphenes in subjects with advanced photoreceptor degeneration. These perceptual responses, and the electrically evoked responses recorded from the scalp in response to such stimuli, have been interpreted as evidence that inner retinal cells in subjects with photoreceptor degeneration retain at least partial function. However, the phosphenes elicited with a contact lens electrode or by electrical stimulation of the optic nerve lack well defined shape or localization.

The production of a small localized visual percept that might allow the generation of a two-dimensional array of phosphenes to provide "pixelized visual input" has been explored in both acute and chronic studies of blind subjects. Even partial restoration of vision in subjects blind from photoreceptor degeneration has been shown to be important.

SUMMARY

According to a first aspect, an external testing device for simulation of a retinal stimulation system implanted on a subject is disclosed, the external testing device comprising: a test board unit to simulate electrical functionalities of the retinal stimulation system; and a test display unit connected to an output of the test board unit, the test display unit visually monitoring the signals processed through the test board unit, thus simulating a visual effect on the subject of the signals.

According to a second aspect, a method for externally simulating a retinal stimulation system implanted on a subject is disclosed, the method comprising: selecting a test board unit to simulate electrical functionalities of the retinal stimulation system; and selecting a test display unit for visually monitoring the signals processed through the test board unit, thus simulating a visual effect on the subject of the signals.

According to a third aspect, a method for simulating a retinal stimulation system implanted on a subject is disclosed, the method comprising: providing a video camera associated with a pair of glasses; capturing an image through the video camera; sending the image to a video processing unit; converting the image to a digital image; processing the digital image to obtain a processed digital image; and presenting the processed digital image to a test array system (80) adapted to simulate electrical functionalities of the retinal stimulation system and adapted to visually display signals associated with the processed digital image.

Further embodiments are shown in the specification, drawings and claims of the present application.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION

The present disclosure is concerned with an apparatus and a method for indication of visual stimulation. In particular, the present disclosure provides a method for verifying that a proper visual stimulation is applied to a visual prosthesis (i.e. device) implanted in an individual patient (i.e. subject) to create artificial vision.

Figure 1:
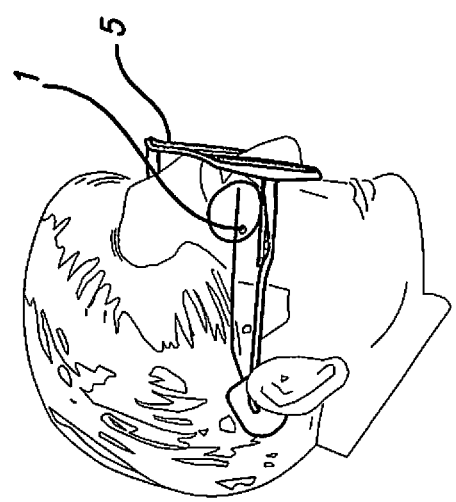
FIG. 1 shows a visual prosthesis apparatus according to the present disclosure.

FIG. 1 shows a visual prosthesis apparatus. The visual apparatus provides an exemplary implantable Retinal Stimulation System 1 and a video capture/transmission apparatus embodied in Glasses 5. The exemplary Retinal Stimulation System 1 is shown in more detail in FIGS. 2 and 3 and the exemplary Glasses 5 are shown in more detail in FIGS. 4 and 5.

The Retinal Stimulation System 1 is further disclosed in U.S. application Ser. No. 11/207,644, filed Aug. 19, 2005 for "Flexible Circuit Electrode Array" by Robert J. Greenberg, et. al. incorporated herein by reference, and is intended for use in subjects with retinitis pigmentosa.

Figure 2:
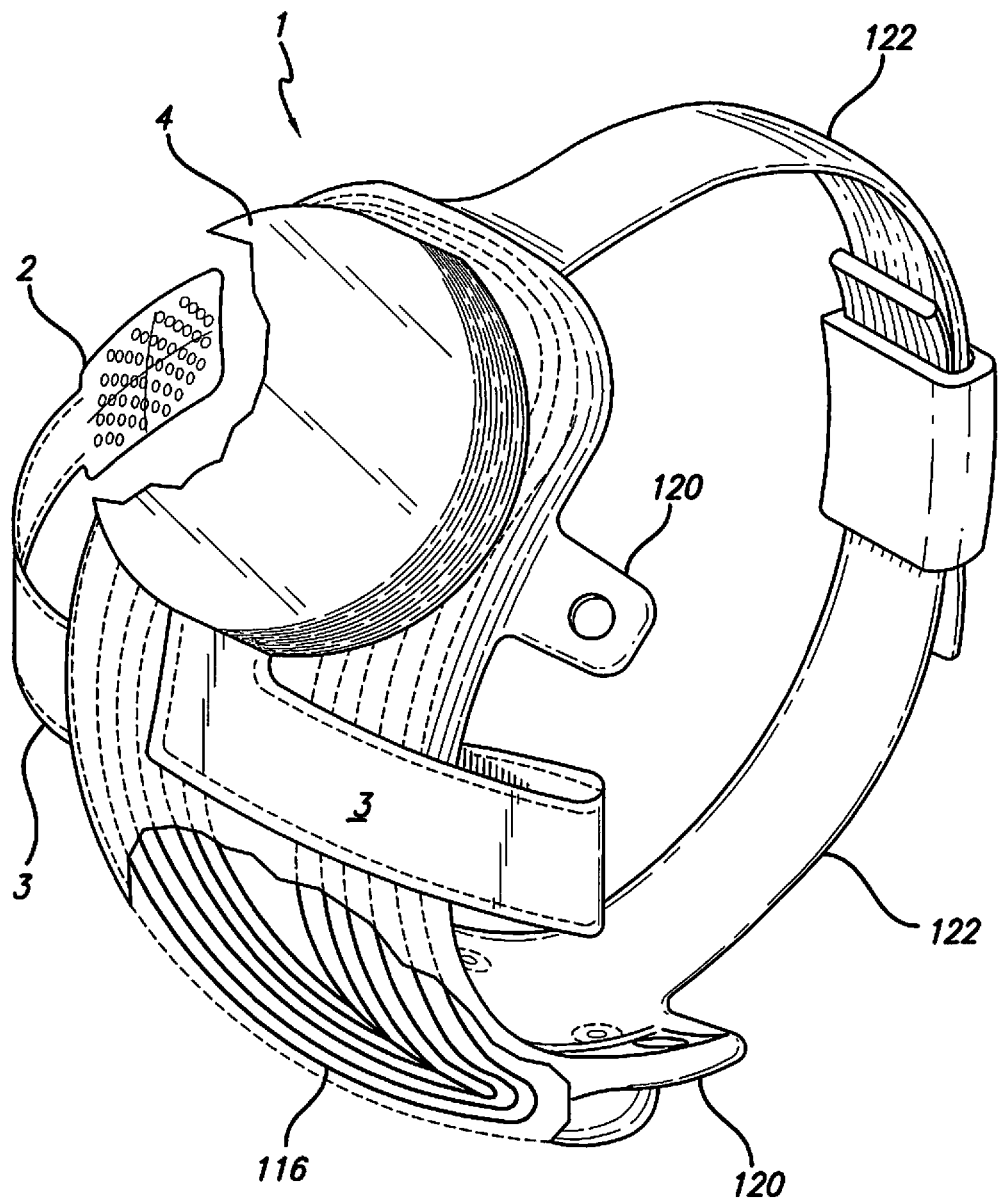
FIGS. 2-3 show a Retinal Stimulation System according to the present disclosure.
Figure 3:
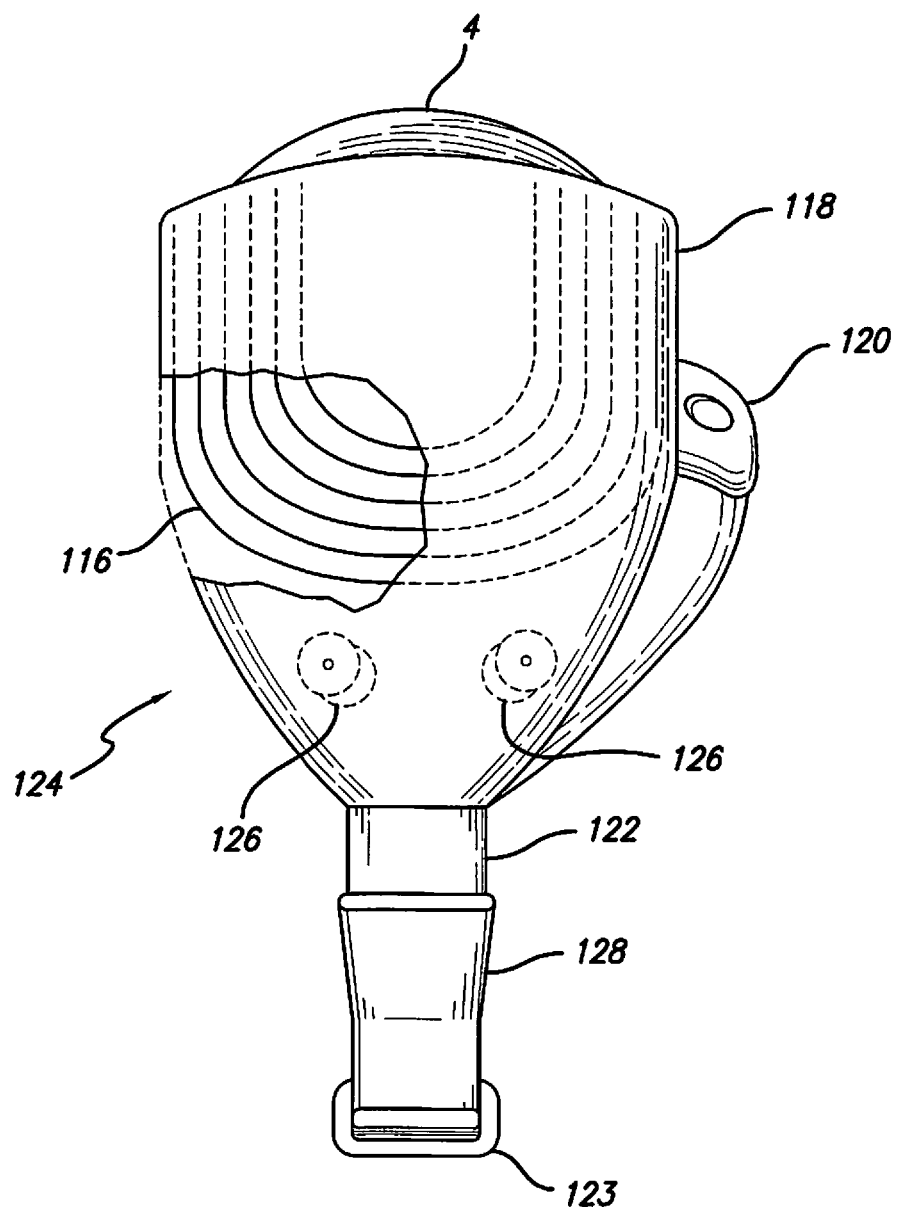

The exemplary Retinal Stimulation System 1, shown in FIGS. 2 and 3, is an implantable electronic device containing an inductive coil 116, an electrode array 2 that is electrically coupled by a cable 3 that pierces sclera of the subject's eye to an electronics package 4, external to the sclera. The Retinal Stimulation System 1 is designed, for example, to elicit visual percepts in blind subjects with retinitis pigmentosa.

Human vision provides a field of view that is wider than it is high. This is partially due to fact that we have two eyes, but even a single eye provides a field of view that is approximately 90° high and 140° to 160° degrees wide. It is therefore, advantageous to provide a flexible circuit electrode array 2 that is wider than it is tall. This is equally applicable to a cortical visual array. In which case, the wider dimension is not horizontal on the visual cortex, but corresponds to horizontal in the visual scene.

Figure 6:
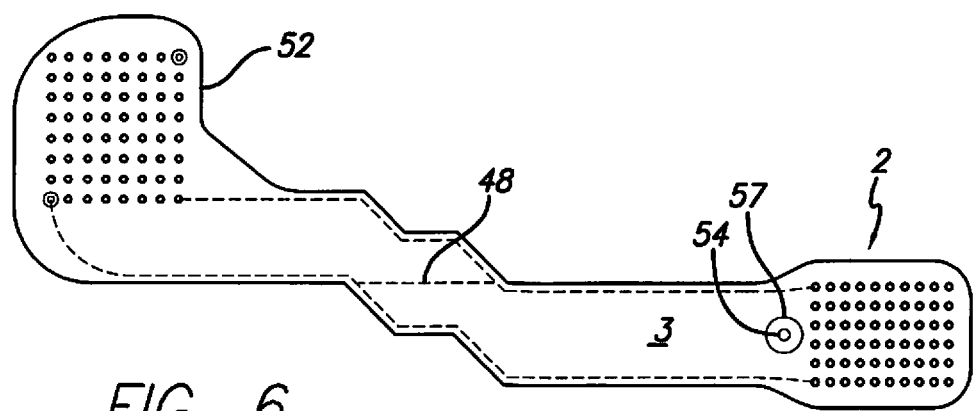
FIG. 6 shows a flexible circuit electrode array according to the present disclosure.

FIG. 6 shows the flexible circuit electrode array 2 prior to folding and attaching to the electronics package 4. A flexible circuit cable 3 is shown in the Figure. At one end of the flexible circuit cable 3 is an interconnection pad 52 for connection to the electronics package 4. At the other end of the flexible circuit cable 3 is the flexible circuit electrode array 2. Further, an attachment point 54 is provided near the flexible circuit electrode array 2. A retina tack (not shown) is placed through the attachment point 54 to hold the flexible circuit electrode array 2 to the retina. A stress relief 57 may be provided surrounding the attachment point 54. The stress relief 57 may be made of a softer polymer than the flexible circuit, or it may include cutouts or thinning of the polymer to reduce the stress transmitted from the retina tack to the flexible circuit electrode array 2. The flexible circuit cable 3 is formed in a dog leg pattern so than when it is folded at fold 48 it effectively forms a straight flexible circuit cable 3 with a narrower portion at the fold 48 for passing through the sclerotomy.

The electronics package 4 of FIGS. 2 and 3 can be electrically coupled to the inductive coil 116. In one aspect, the inductive coil 116 is made from wound wire. Alternatively, the inductive coil 116 may be made from a thin film polymer sandwich with wire traces deposited between layers of thin film polymer. The electronics package 4 and the inductive coil 116 are held together by a molded body 118 shown in FIG. 3. As also shown in FIG. 3, the molded body 118 may also include suture tabs 120 shown in FIG. 3. The molded body narrows to form a strap 122 which surrounds the sclera and holds the molded body 118, inductive coil 116, and electronics package 4 in place. The molded body 118, suture tabs 120 and strap 122 are preferably an integrated unit made of silicone elastomer. Silicone elastomer can be formed in a pre-curved shape to match the curvature of a typical sclera. Furthermore, silicone remains flexible enough to accommodate implantation and to adapt to variations in the curvature of an individual sclera. In one aspect, the inductive coil 116 and molded body 118 are oval shaped, and in this way, a strap 122 can better support the oval shaped coil.

The eye moves constantly. The eye moves to scan a scene and also has a jitter motion to prevent image stabilization. Even though such motion is useless in the blind, it often continues long after a person has lost their sight. Thus, in one embodiment of the present disclosure, the entire Retinal Stimulation System 1 of the prosthesis is attached to and supported by the sclera of a subject. By placing the device under the rectus muscles with the electronics package in an area of fatty tissue between the rectus muscles, eye motion does not cause any flexing which might fatigue, and eventually damage, the device.

FIG. 3 shows a side view of the Retinal Stimulation System 1, in particular, emphasizing the fan tail 124. When the retinal prosthesis is implanted, the strap 122 is passed under the eye muscles to surround the sclera. The inductive coil 116 and molded body 118 should also follow the strap under the lateral rectus muscle on the side of the sclera. The Retinal Stimulation System 1 of the visual prosthesis apparatus is very delicate. It is easy to tear the molded body 118 or break wires in the inductive coil 116. In order to allow the molded body 118 to slide smoothly under the lateral rectus muscle, the molded body is shaped in the form of a fan tail 124 on the end opposite the electronics package 4. Element 123 shows a retention sleeve, while elements 126 and 128 show holes for surgical positioning and a ramp for surgical positioning, respectively.

Figure 4:
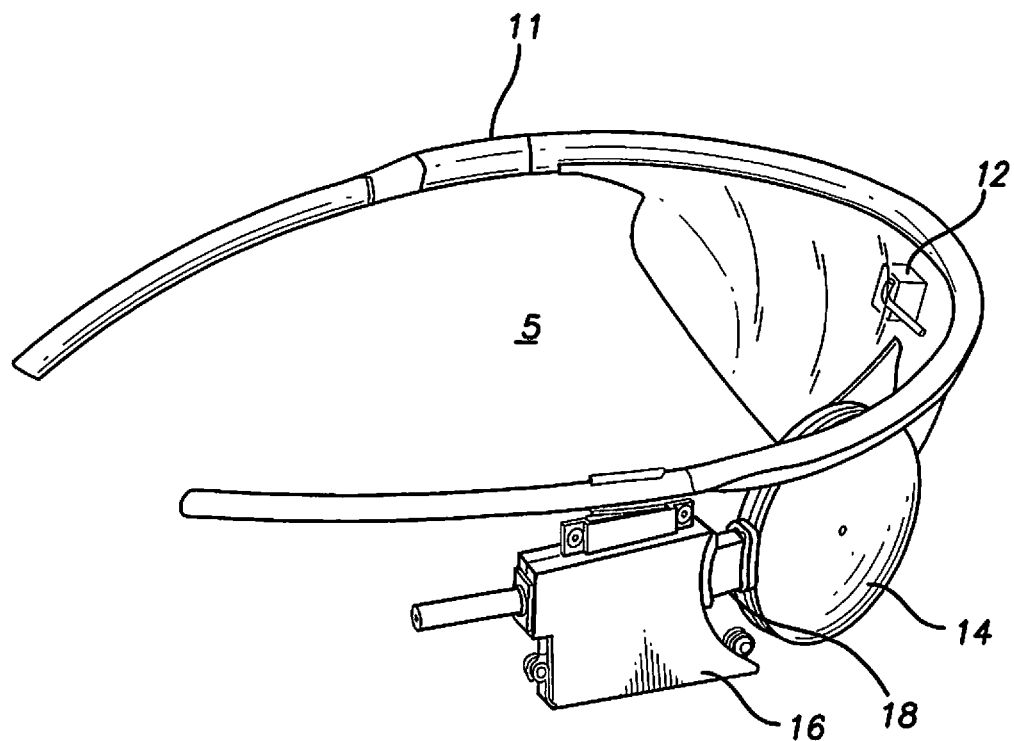
FIGS. 4-5 show a video capture/transmission apparatus according to the present disclosure.
Figure 5:
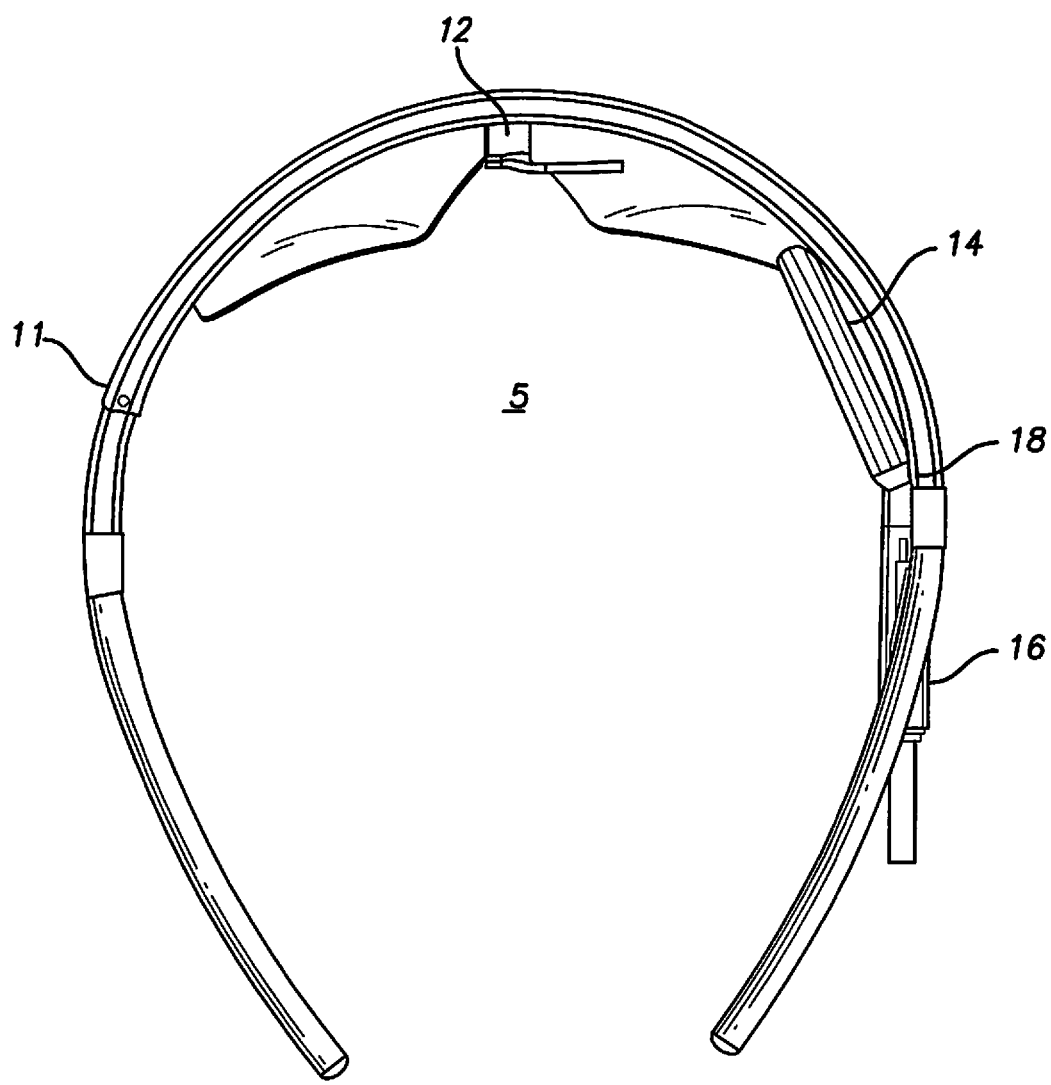

Referring to FIGS. 4-5, the Glasses 5 may comprise, for example, a frame 11 holding a camera 12, an external coil 14 and a mounting system 16 for the external coil 14. The mounting system 16 may also enclose the RF circuitry. In this configuration, the video camera 12 captures live video. The video signal is sent to an external Video Processing Unit (VPU) 20 (shown in FIG. 7 and discussed below), which processes the video signal and subsequently transforms the processed video signal into electrical stimulation patterns or data. The electrical stimulation data are then sent to the external coil 14 which sends both the data and power via radio-frequency (RF) telemetry to the coil 116 of the Retinal Stimulation System 1. The coil 116 receives the RF commands which control an application specific integrated circuit (ASIC) which in turn delivers stimulation to the retina of the subject via a thin film electrode array (TFEA). In one aspect of an embodiment, light amplitude is recorded by the camera 12. The VPU 20 may use a logarithmic encoding scheme to convert the incoming light amplitudes into the electrical stimulation patterns or data. These electrical stimulation patterns or data may then be passed on to the Retinal Stimulation System 1, which results in the retinal cells being stimulated via the electrodes in the electrode array 2. In one exemplary embodiment, the electrical stimulation patterns or data being transmitted by the external coil 14 is binary data.

Figure 7:
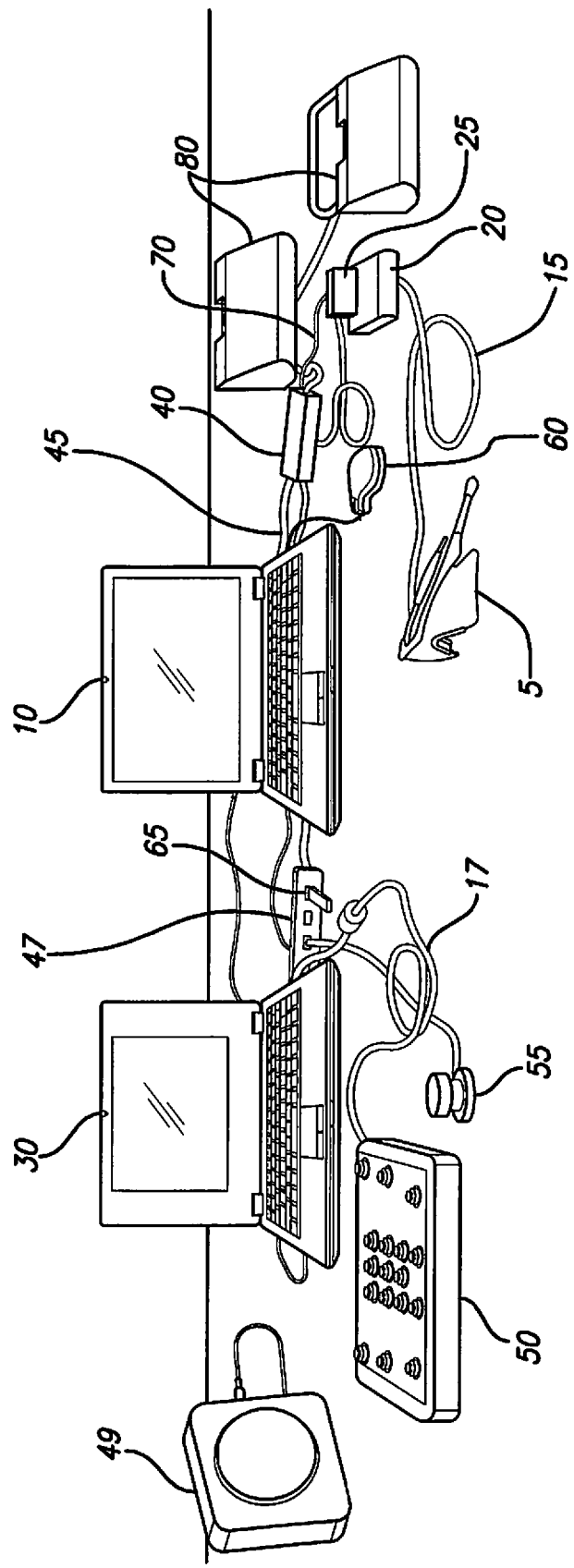
FIG. 7 shows components of a fitting system according to the present disclosure.

Referring to FIG. 7, a Fitting System (FS) may be used to configure and optimize the visual prosthesis 3 of the exemplary Retinal Stimulation System 1. The Fitting System is fully described in the related application U.S. application Ser. No. 11/796,425, filed on Apr. 27, 2007, which is incorporated herein by reference in its entirety.

The Fitting System may comprise custom software with a graphical user interface running on a dedicated laptop computer 10. Within the Fitting System are modules for performing diagnostic checks of the implant, loading and executing video configuration files, viewing electrode voltage waveforms, and aiding in conducting psychophysical experiments. A video module can be used to download a video configuration file to the Video Processing Unit (VPU) 20 discussed above and store it in non-volatile memory to control various aspects of video configuration, e.g. the spatial relationship between the video input and the electrodes. The software can also load a previously used video configuration file from the VPU 20 for adjustment.

The Fitting System can be connected to the Psychophysical Test System (PTS), located for example on a dedicated laptop 30, in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

The stimulation parameters are checked to ensure that maximum charge per phase limits, charge balance, and power limitations are met before the test stimuli are sent to the VPU 20 to make certain that stimulation is safe.

Using the psychophysics module, important perceptual parameters such as perceptual threshold, maximum comfort level, and spatial location of percepts may be reliably measured. Based on these perceptual parameters, the fitting software enables custom configuration of the transformation between video image and spatio-temporal electrode stimulation parameters in an effort to optimize the effectiveness of the retinal prosthesis for each subject.

The Fitting System laptop 10 of FIG. 7 may be connected to the VPU 20 using an optically isolated serial connection adapter 40. Because it is optically isolated, the serial connection adapter 40 assures that no electric leakage current can flow from the Fitting System laptop 10.

As shown in FIG. 7, the following components may be used with the Fitting System according to the present disclosure. A Video Processing Unit (VPU) 20 for the subject being tested, a Charged Battery 25 for VPU 20, Glasses 5, a Fitting System (FS) Laptop 10, a Psychophysical Test System (PTS) Laptop 30, a PTS CD (not shown), a Communication Adapter (CA) 40, a USB Drive (Security) (not shown), a USB Drive (Transfer) 47, a USB Drive (Video Settings) (not shown), a Patient Input Device (RF Tablet) 50, a further Patient Input Device (Jog Dial) 55, Glasses Cable 15, CA-VPU Cable 70, CFS-CA Cable 45, CFS-PTS Cable 46, Four (4) Port USB Hub 47, Mouse 60, Test Array system 80, Archival USB Drive 49, an Isolation Transformer (not shown), adapter cables (not shown), and an External Monitor (not shown).

With continued reference to FIG. 7, the external components of the Fitting System may be configured as follows. The battery 25 is connected with the VPU 20. The PTS Laptop 30 is connected to FS Laptop 10 using the CFS-PTS Cable 46. The PTS Laptop 30 and FS Laptop 10 are plugged into the Isolation Transformer (not shown) using the Adapter Cables (not shown). The Isolation Transformer is plugged into the wall outlet. The four (4) Port USB Hub 47 is connected to the FS laptop 10 at the USB port. The mouse 60 and the two Patient Input Devices 50 and 55 are connected to four (4) Port USB Hubs 47. The FS laptop 10 is connected to the Communication Adapter (CA) 40 using the CFS-CA Cable 45. The CA 40 is connected to the VPU 20 using the CA-VPU Cable 70. The Glasses 5 are connected to the VPU 20 using the Glasses Cable 15.

Figure 8:
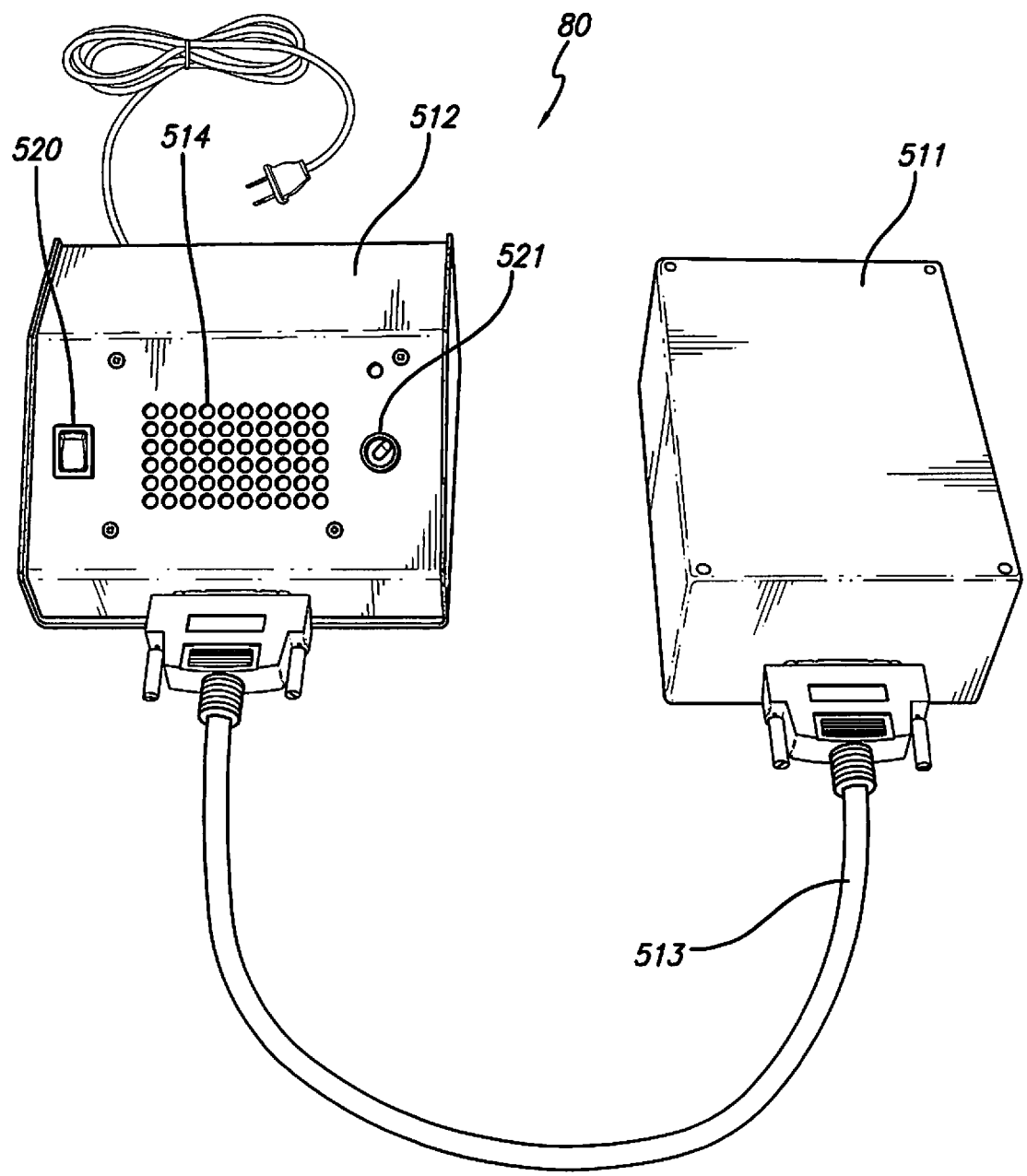
FIG. 8 shows a test array system according to the present disclosure.

Referring to FIG. 8, the Test Array system 80 according to the present disclosure (already briefly discussed with reference to FIG. 7) may be used to verify that a proper visual stimulation is being applied to the Retinal Stimulation System 1 by the external coil 14. The Test Array system 80 may comprise a test board unit 511 and a display unit 512 interconnected by cable 513. The person skilled in the art will understand that the Test Array system 80 is not limited to having the test board unit 511 separate from the display unit 512 as shown in FIG. 8. In particular, the two units can also be combined into a single unit.

After the Retinal Stimulation System 1 is implanted into the patient it may be advantageous to externally verify that the data transmitted by the external coil 14 to the Retinal Stimulation System 1 is correct without placing any additional circuitry into the patient. The exemplary Test Array system 80 may be used to make such verification.

Figure 9:
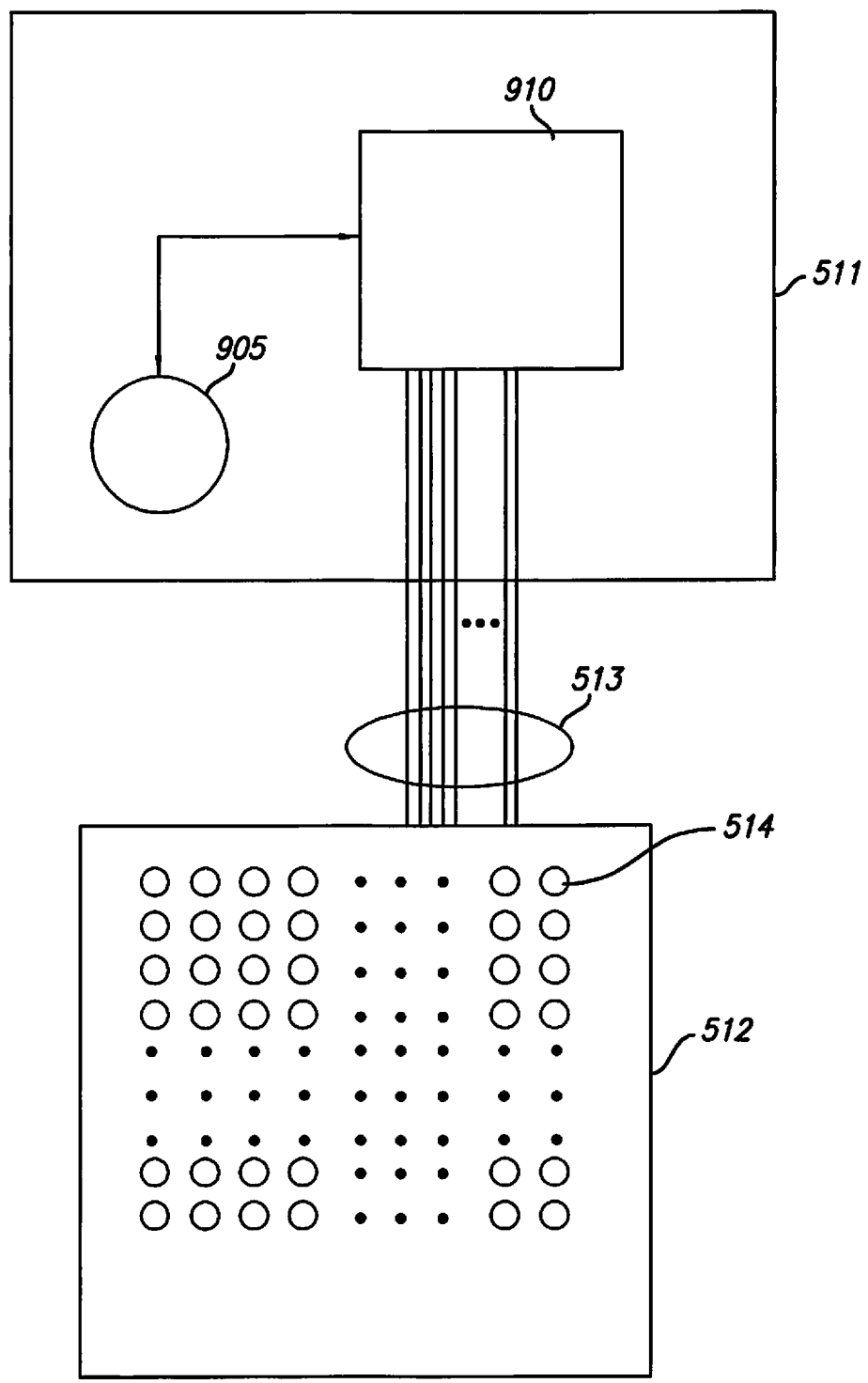
FIG. 9 shows an exemplary test array system according to the present disclosure.

In one exemplary embodiment according to the present application, the test board unit 511 contains the necessary electronics (ASIC chip, receiving coil etc) to allow simulation of the electrical functionality of the Retinal Stimulation System 1 described above. To verify that data is being transmitted correctly, the external coil 14 may be placed near or in contact with the test board unit 511. FIG. 9 shows a test coil 905 for transmitting data/power, received from the external coil 14, to the Application Specific Integrated Circuit (ASIC) 910 of the test board unit 511. In operation, the ASIC 910 translates the data from the external coil 14 into current (pulse) amplitudes that are transmitted to the LEDs 514 in the display unit 512 through the cable 513. With the help of the VPU 20 the external coil 14 may be used to communicate with the test board unit 511 as if it is communicating with the Retinal Stimulation System 1. As far as the external coil 14 is concerned, the test board unit 511 is the Retinal Stimulation System 1. However, instead of transmitting data to the patient's implant, the signals from the external coil 14 may be monitored on the display unit 512. One skilled in the art will appreciate that other electronics (switches, amplifiers, etc.) may be incorporated into the test board unit 511 and the display unit 512 without departing from the spirit and scope of the invention.

The display unit 512 may contain LEDs 514 or any other types of displays (CRT, video, LCD etc.) to help monitor the signals from the external coil 14. In one exemplary embodiment according to the present application, each LED 514 may correspond to a specific electrode in the electrode array 2. The display unit 512 may also contain a power switch 520 to switch on the power supply to the unit 512, a test button 521 to turn on all the LEDs 514 and to test the proper operation of the LEDs 514 and their driver circuit.

In one embodiment, the graphical user interface of the Fitting System shown in FIG. 7 together with the Test Array system 80 may be used to make sure that the external coil 14 is able to transmit appropriate signals to each electrode in the electrode array 2.

In one exemplary embodiment, using Direct Stimulation option in the PTS system disclosed above, an experimenter may utilize the Test Array system 80 to (1) design a stimulation wave form for a single or multiple electrodes and (2) conduct manual testing of the the external coil 14.

Figure 10:
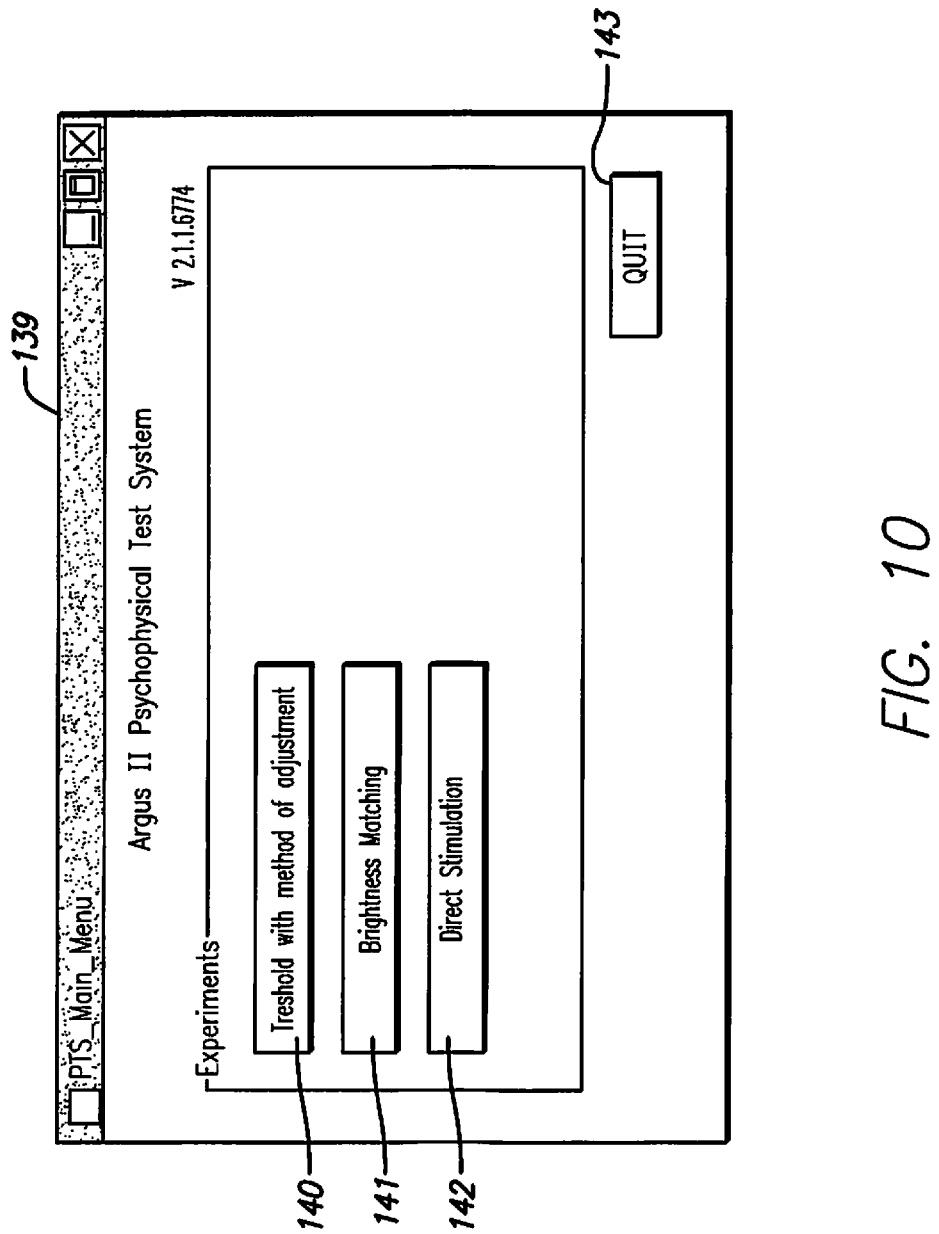
FIG. 10 shows a Psychophysical Test System (PTS) main screen.

The Psychophysical Test System (PTS) main screen 139, shown in FIG. 10, has four options: 1) 'Threshold with method of adjustment' 140, 2) 'Brightness matching' 141, 3) 'Direct Stimulation' 142, and 4) 'Quit' 143.

Figure 11:
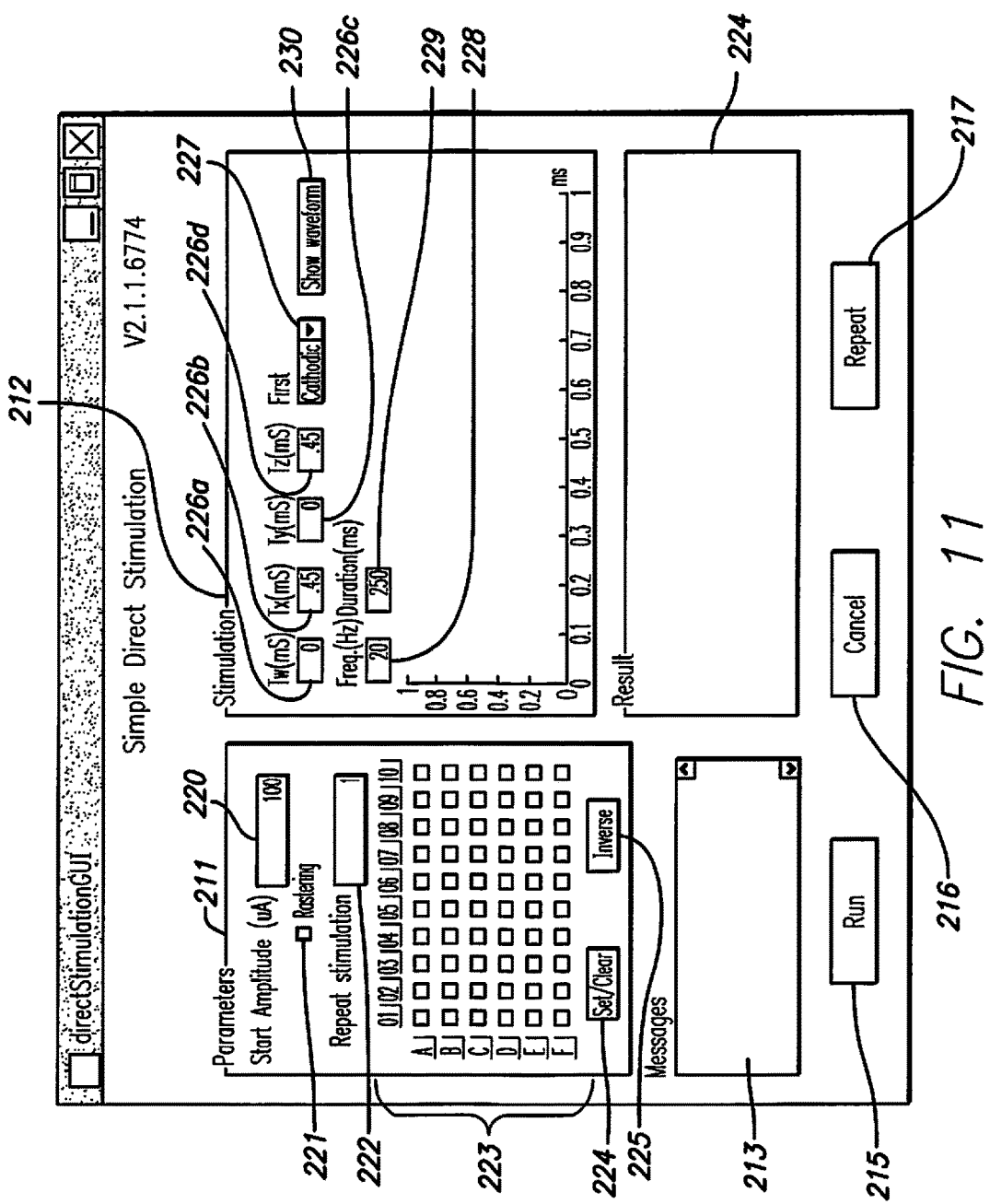
FIG. 11 shows a 'Simple Direct Stimulation' computer screen.
Figure 12:
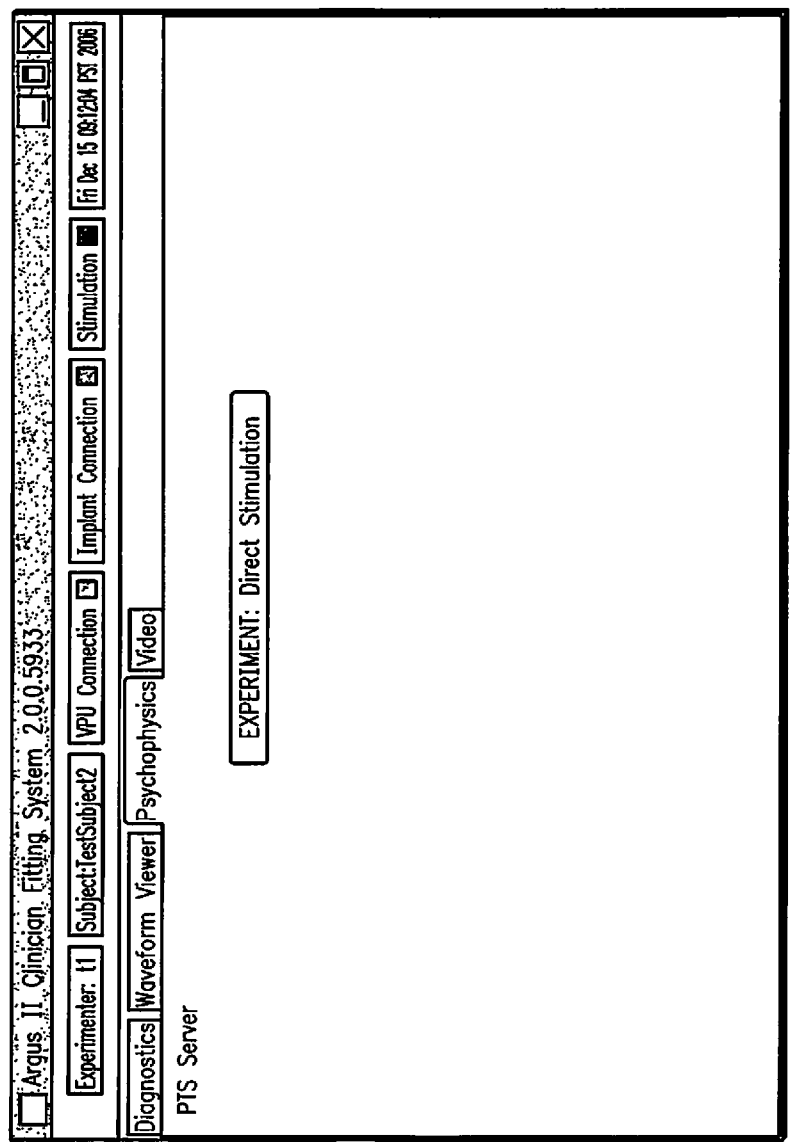
FIG. 12 shows an 'EXPERIMENT: direct stimulation' message box.

A 'Direct Stimulation' screen 210 shown in FIG. 11 appears when the 'Direct Stimulation' button 142 of FIG. 10 is selected from the PTS Main Menu Screen 139 of FIG. 10. The 'Direct Stimulation' screen 210 may also contain 1) 'Parameters' panel 211, 2) 'Stimulation' panel 212, 3) 'Message' panel 213, and 4) 'Result' panel 214. During a Direct Stimulation experiment, the PTS Server screen on the FS Laptop 10 may display "RUNNING: Direct Stimulation" as shown in FIG. 12.

Configuration parameters may be entered for the experiment as described below with reference to FIG. 11.

Starting stimulation amplitude(s) (μA) for each of the selected electrodes may be entered into a 'Start Amplitude' window 220 of the 'Parameters' panel 211. 'Rastering' 221 may be used to stagger the start times that electrodes are stimulated. When this option is not selected, all electrodes are stimulated simultaneously.

The number of times a stimulation will be repeated may be entered into a 'Repeat Stimulation' window 222 of the 'Parameters' panel 211. The time delay between successive repetitions may be approximately 0.5 seconds.

The electrodes to be stimulated can be selected from the 'Electrodes' windows 223 of the 'Parameters' panel 211. The electrodes may be individually selected by clicking individual boxes. Complete rows of electrodes may be selected or de-selected by clicking on the alphabetic button (A-F). Complete columns of electrodes may be selected or de-selected by clicking on the numeric button (01-10). All electrodes can be selected by using the 'Set/Clear' button 224. The inverse of the selected electrodes can be achieved by clicking on the 'Inverse' button 225.

Figure 13:
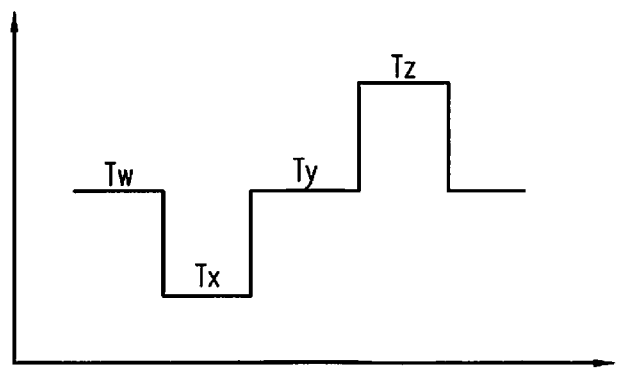
FIG. 13 shows a waveform related to FIG. 12.

A Pulse Width (ms) may be entered into windows 226a-d of the 'Stimulation' panel 212. A desired time between start of the effective stimulation window and initiation of the first phase may be entered into a Tw window 226a. The duration of the first phase may be entered into a Tx window 226b. The desired time between the end of the first phase and the beginning of the second phase may be entered into a Ty window 226c. Duration of the second phase may be entered into a Tz window 226d. FIG. 13 depicts a possible waveform of the numbers entered into windows 226a-d.

The frequency of how many times per second the waveform shown in FIG. 13 will be repeated may be entered into a 'Frequency' window 228 of the 'Stimulation' panel 212. A desired length of each stimulation in milliseconds (i.e. the length of stimulation at a given test amplitude) may be entered into a 'Duration' window 229 of the 'Stimulation' panel 212. Selection of whether the first phase is a negative (cathodic) current phase or a positive (anodic) current phase may be performed using the first window 227 of the 'Stimulation' panel 212. The 'Show Waveform' button 230 may be used to produce a graph that plots the waveform of the complete stimulus for a trial. The 'Run' button 215 may be used to proceed with the experiment.

Figure 14:
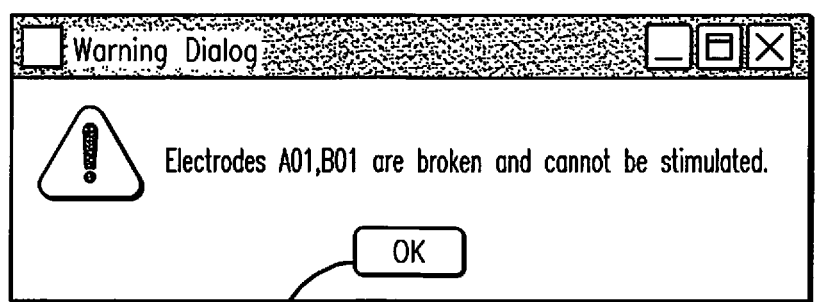
FIG. 14 shows a warning dialog box.

After the 'Run' button 215 or 'Show Waveform' button 230 are activated, the parameters may be checked against safety requirements of the system. If any of the parameters violates safety limits, a message box will be displayed and the experimenter will need to change the configuration parameters. Common errors may include broken/shorted electrodes, start amplitudes which exceed a maximum charge per phase limit (or the maximum total instantaneous current limit). For example, if there are any broken electrodes, the popup message shown in FIG. 14 may be displayed on the screen. While the experiment is running, the 'Result' screen 214 of FIG. 11 will indicate that stimulation is in progress. The 'Cancel' button 216 of FIG. 11 may be used to cancel Stimulation. A message (not shown) may appear indicating that stimulation was stopped by request.

Figure 15:
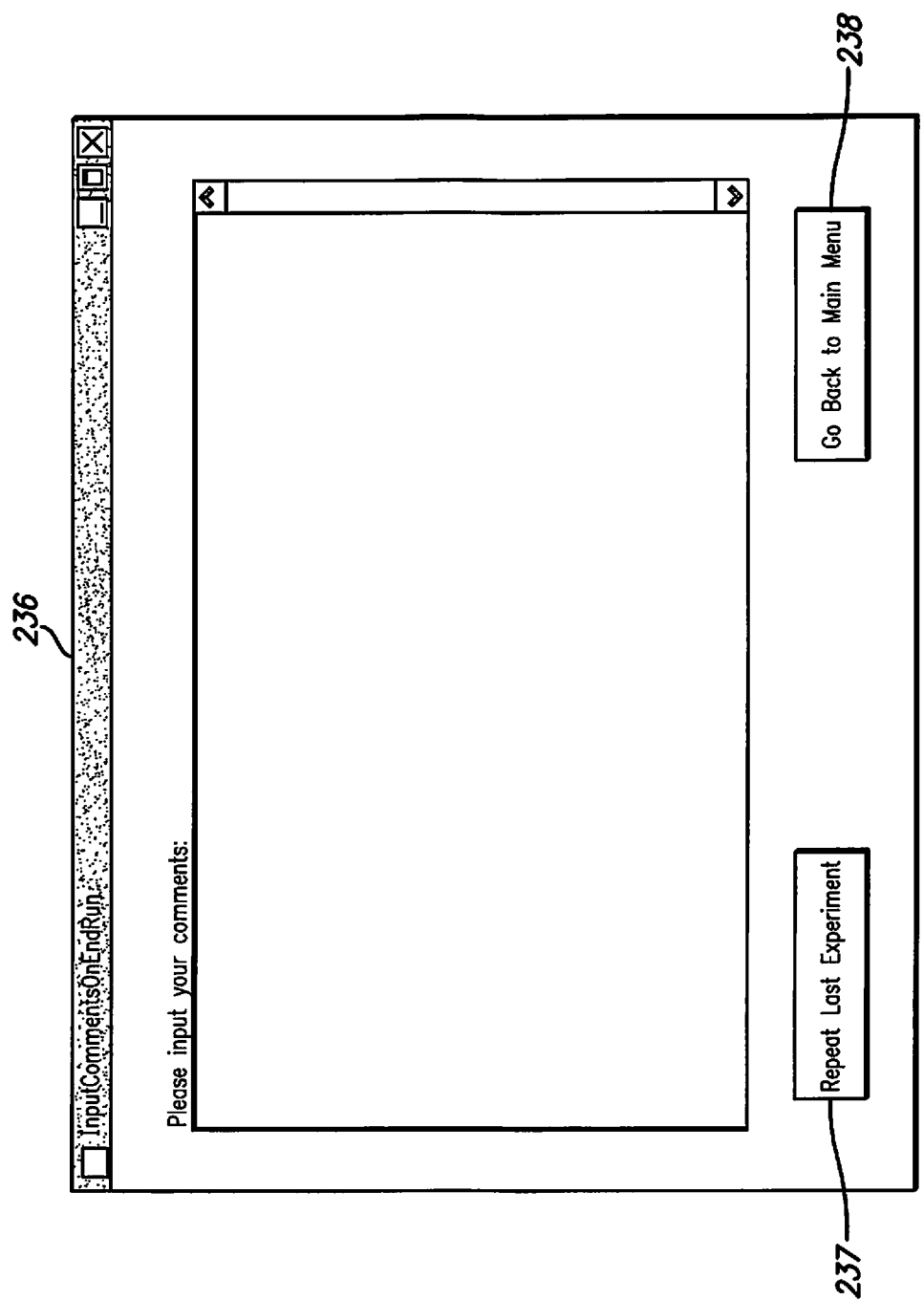
FIG. 15 shows an 'Input Your Comments' message box.

If stimulation has ended normally, a Comment screen 236 shown in FIG. 15 may be displayed. The Comment screen 236 contains two buttons, 'Repeat Last Experiment' 237 and 'Go Back to Main Menu' 238. If Repeat Last Experiment 237 is chosen, the experimenter will be returned to the main Direct Stimulation screen 210 with the Parameters from the last experiment and the experimenter can modify and repeat the experiment. If 'Go Back to Main Menu' 238, is chosen, the experimenter will be returned to the main PTS menu 139.

In one exemplary embodiment, by selecting all the electrodes with the button 224; by selecting "Rastering" 221; by selecting the "Start Amplitude" 220 to be 10 μA; by selecting the Tx 226b, Ty 226c, Tz 226d and Tw 226a to be 0.45 ms; by choosing Frequency 228 to be 60 Hz; and by choosing Duration 229 to be 250 ms it is possible to make sure that the external coil 14 transmits data to all the electrodes in the electrode array 2 if all the LED 514 are lit continuously for the duration of the stimulus.

In another embodiment, by selecting all the electrodes with the button 224; by selecting "Rastering" 221; by selecting the "Start Amplitude" 220 to be 30 μA; by selecting the Tx 226b, Ty 226c, Tz 226d and Tw 226a to be 0.45 ms; by choosing Frequency 228 to be 60 Hz; and by choosing Duration 229 to be 250 ms it is possible to make sure that the external coil 14 transmits data at higher power to all the electrodes in the electrode array 2 if all the LED 514 are lit continuously and brighter compared to the above embodiment.

In one exemplary embodiment, the Test Array system 80 may be reconfigurable so as to be able to verify that a proper visual stimulation is being applied to an implant other than the Retinal Stimulation System 1. The Test Array system 80 may be reconfigured either using the graphical user interface of the Fitting System shown in FIG. 7 or through a hard-wired switch (not shown).

The following concepts are supported by the present application:

Concept 1. An external testing device for simulation of a retinal stimulation system implanted on a subject, comprising:

a test board unit to simulate electrical functionalities of the retinal stimulation system; and a test display unit connected to an output of the test board unit, the test display unit visually monitoring the signals processed through the test board unit, thus simulating a visual effect on the subject of the signals.

Concept 2. The external testing device of Concept 1, wherein the test board unit and the test display unit are two separate components.

Concept 3. The external testing device of Concept 1, wherein the test board unit and the test display unit are part of a single component.

Concept 4. The external testing device of Concept 1, further comprising an external coil connectable with the test board unit and adapted to send signals to the test board unit.

Concept 5. The external testing device of Concept 4, wherein the external coil is configured to receive stimulation patterns from a video processing unit, wherein the stimulation patterns are based on visual signals processed by the video processing unit.

Concept 6. The external testing device of Concept 1, wherein the test display unit comprises a plurality of visualization devices.

Concept 7. The external testing device of Concept 6, wherein each visualization device of the plurality of visualization devices corresponds to a specific electrode of an array of electrodes of the retinal stimulation system.

Concept 8. The external testing device of Concept 1, wherein the test display unit comprises a power switch to switch on power supply to the test display unit.

Concept 9. The external testing device of Concept 6, wherein the test display unit comprises a test button to turn on all visualization devices of the plurality of visualization devices.

Concept 10. The external testing device of Concept 1, wherein the test board unit is configured to process logarithmic electrical signals.

Concept 11. The external testing device of Concept 4, wherein the external coil is adapted to send logarithmic electrical signals to the test board unit.

Concept 12. The external testing device of Concept 10, wherein the test board unit is configured to process the logarithmic electrical signals.

Concept 13. The external testing device of Concept 1, wherein the test board unit is adapted to simulate electrical functionalities of another retinal stimulation system, wherein the signals to the retinal stimulation system do not correspond to the signals to the another retinal stimulation system.

Concept 14. A method for externally simulating a retinal stimulation system implanted on a subject, the method comprising:
providing a test board unit to simulate electrical functionalities of the retinal stimulation system; and
providing a test display unit for visually monitoring the signals processed through the test board unit, thus simulating a visual effect on the subject of the signals.

Concept 15. The method of Concept 14, wherein the test board unit and the test display unit are two separate components.

Concept 16. The method of Concept 14, wherein the test board unit and the test display unit are part of a single component.

Concept 17. The method of Concept 14, wherein the signals processed through the test board unit are from an external coil.

Concept 18. The method of Concept 17, further comprising selecting a video processing unit adapted to process visual signals and transform the visual signals to stimulation patterns to be sent to the external coil.

Concept 19. The method of Concept 14, wherein the test display unit comprises a plurality of visualization devices.

Concept 20. The method of Concept 19, wherein each visualization device of the plurality of visualization devices corresponds to a specific electrode of an array of electrodes of the retinal stimulation system.

Concept 21. The method of Concept 14, wherein the test display unit comprises a power switch to switch on power supply to the test display unit.

Concept 22. The method of Concept 19, wherein the test display unit comprises a test button to turn on all visualization devices of the plurality of visualization devices.

Concept 23. The method of Concept 14, wherein the test board unit is configured to process logarithmic electrical signals.

Concept 24. The method of Concept 17, wherein the signals from the external coil are logarithmic electrical signals.

Concept 25. The external testing device of Concept 23, wherein the test board unit is configured to process the logarithmic electrical signals.

Concept 26. The method of Concept 14, wherein the test board unit is adapted to simulate electrical functionalities of another retinal stimulation system, wherein the signals to the retinal stimulation system do not correspond to the signals to the another retinal stimulation system.

Concept 27. A method for simulating a retinal stimulation system implanted on a subject, the method comprising:
providing a video camera associated with a pair of glasses;
capturing an image through the video camera;
sending the image to a video processing unit;
converting the image to a digital image;
processing the digital image to obtain a processed digital image; and
presenting the processed digital image to a test array system adapted to simulate electrical functionalities of the retinal stimulation system and adapted to visually display signals associated with the processed digital image.

Concept 28. The method of Concept 27, wherein the test array system comprises:
a test board unit for processing the signals associated with the processed digital image; and
a test display unit for visually monitoring the signals processed through the test board unit.

Accordingly, what has been shown is an improved method of verifying that a proper visual stimulation is being applied to the implant device. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An external testing device for simulation of a implantable visual prosthesis stimulation system implanted on a subject, comprising:
A non-implantable wireless receiver for wirelessly receiving visual information signals generated from a video processing unit, the non-implantable wireless receiver simulating and mimicking electrical functionalities of the implantable visual prosthesis stimulation system; and
a non-implantable display unit, viewable by a clinician, connected to an output of the non-implantable wireless receiver, the non-implantable display unit visually monitoring the visual information signals wirelessly received through the non-implantable wireless receiver and displaying the visual information signals using image elements, in an array pattern simulating and mimicking an array of electrodes of the implantable visual prosthesis stimulation system, each image element corresponding to a specific electrode of the array of electrodes of the implantable visual prosthesis stimulation system, to test the function of the video processing unit.

2. The external testing device of claim 1, wherein the non-implantable wireless receiver and the non-implantable display unit are two separate components.

3. The external testing device of claim 1, wherein the non-implantable wireless receiver and the non-implantable display unit are part of a single component.

4. The external testing device of claim 1, further comprising an external coil connectable with the non-implantable wireless receiver and adapted to send the visual information signals to the non-implantable wireless receiver.

5. The external testing device of claim 4, wherein the external coil is configured to receive stimulation patterns from the video processing unit, wherein the stimulation patterns are based on visual information signals processed by the video processing unit.

6. The external testing device of claim 1, wherein the non-implantable display unit comprises a plurality of visualization devices, each visualization device displaying one image element.

7. The external testing device of claim 6, wherein each visualization device of the plurality of visualization devices corresponds to a specific electrode of an array of electrodes of the visual prosthesis stimulation system.

8. The external testing device of claim 6, wherein the non-implantable display unit comprises a power switch to switch on power supply to the non-implantable display unit and a test button to turn on all visualization devices of the plurality of visualization devices.

9. The external testing device of claim 1, wherein the non-implantable wireless receiver is adapted to simulate electrical functionalities of another visual prosthesis stimulation system, wherein the visual information signals to the visual prosthesis stimulation system do not correspond to the signals to the another visual prosthesis stimulation system.

10. A method for externally simulating a visual prosthesis stimulation system implanted on a subject and testing the function of a video processing unit, the method comprising:
wirelessly receiving visual information signals generated from a video processing unit using a non-implantable wireless receiver, the non-implantable wireless receiver simulating electrical functionalities of the visual prosthesis stimulation system;
visually monitoring the visual information signals received through the non-implantable wireless receiver using a non-implantable display unit;
displaying the visual information signals using image elements in an array pattern simulating and mimicking an array of electrodes of the implantable visual prosthesis stimulation system, each image element corresponding to a specific electrode of the array of electrodes of the implantable visual prosthesis stimulation system, to test the function of the video processing unit.

11. The method of claim 10, wherein the non-implantable wireless receiver and the non-implantable display unit are two separate components.

12. The method of claim 10, wherein the non-implantable wireless receiver and the non-implantable display unit are part of a single component.

13. The method of claim 10, wherein the visual information signals processed through the non-implantable wireless receiver are from an external coil.

14. The method of claim 13, further comprising selecting a video processing unit adapted to process visual information signals and transform the visual information signals to stimulation patterns to be sent to the external coil.

15. The method of claim 10, wherein the non-implantable display unit comprises a plurality of visualization devices, each visualization device displaying one image element.

16. The method of claim 15, wherein each visualization device of the plurality of visualization devices corresponds to a specific electrode of an array of electrodes of the visual prosthesis stimulation system.

17. The method of claim 15, wherein the non-implantable display unit comprises a power switch to switch on power supply to the non-implantable display unit and a test button to turn on all visualization devices of the plurality of visualization devices.

18. The method of claim 10, wherein the non-implantable wireless receiver is adapted to simulate electrical functionalities of another visual prosthesis stimulation system, wherein the signals to the visual prosthesis stimulation system do not correspond to the signals to the another visual prosthesis stimulation system.

19. A method for simulating a visual prosthesis stimulation system implanted on a subject, the method comprising:
providing a video camera associated with a pair of glasses;
capturing an image through the video camera;
sending the image to a video processing unit;
converting the image to a digital image;
processing the digital image to obtain a processed digital image;
wirelessly receiving visual information signals generated from a video processing unit using a non-implantable wireless receiver, the non-implantable wireless receiver simulating electrical functionalities of the visual prosthesis stimulation system;
visually monitoring the visual information signals received through the non-implantable wireless receiver using a non-implantable display unit;
displaying the visual information signals using image elements in an array pattern simulating and mimicking an array of electrodes of the implantable visual prosthesis stimulation system, each image element corresponding to a specific electrode of the array of electrodes of the implantable visual prosthesis stimulation system, to test the function of the video processing unit.

20. The method of claim 19, wherein the test array system comprises:
a non-implantable wireless receiver for processing the visual information signals associated with the processed digital image; and
a non-implantable display unit for visually monitoring the visual information signals processed through the test board unit.

* * * * *